(12) United States Patent
Uchida

(10) Patent No.: US 9,042,622 B2
(45) Date of Patent: May 26, 2015

(54) OPTICAL COHERENCE TOMOGRAPHIC APPARATUS, CONTROL METHOD FOR OPTICAL COHERENCE TOMOGRAPHIC APPARATUS AND STORAGE MEDIUM

(75) Inventor: Hiroki Uchida, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 203 days.

(21) Appl. No.: 13/598,753

(22) Filed: Aug. 30, 2012

(65) Prior Publication Data
US 2013/0195336 A1 Aug. 1, 2013

(30) Foreign Application Priority Data
Jan. 26, 2012 (JP) .................................. 2012-014583

(51) Int. Cl.
*A61B 3/10* (2006.01)

(52) U.S. Cl.
CPC ....... *A61B 3/102* (2013.01); *G06T 2207/30041* (2013.01)

(58) Field of Classification Search
None
See application file for complete search history.

(56) References Cited

U.S. PATENT DOCUMENTS

| 6,439,719 | B2 | 8/2002 | Hayashi et al. |
| 7,226,165 | B2 | 6/2007 | Maeda |
| 7,510,282 | B2 | 3/2009 | Ueno et al. |
| 8,794,761 | B2 | 8/2014 | Kobayashi |
| 2002/0018179 | A1 | 2/2002 | Hayashi et al. |
| 2005/0105049 | A1 | 5/2005 | Maeda |
| 2006/0228011 | A1* | 10/2006 | Everett et al. ................. 382/128 |
| 2007/0076217 | A1* | 4/2007 | Baker et al. ................... 356/498 |
| 2007/0195269 | A1* | 8/2007 | Wei et al. ...................... 351/221 |
| 2008/0024721 | A1 | 1/2008 | Ueno et al. |
| 2008/0055543 | A1 | 3/2008 | Meyer et al. |
| 2009/0268020 | A1* | 10/2009 | Buckland et al. ............... 348/78 |
| 2011/0043757 | A1 | 2/2011 | Everett et al. |
| 2011/0228222 | A1* | 9/2011 | Kobayashi ..................... 351/206 |
| 2011/0235050 | A1* | 9/2011 | Bajraszewski et al. ........ 356/497 |
| 2011/0299034 | A1* | 12/2011 | Walsh et al. ................... 351/206 |
| 2012/0113390 | A1* | 5/2012 | Torii et al. ..................... 351/208 |
| 2012/0249769 | A1 | 10/2012 | Naba et al. |
| 2012/0249954 | A1 | 10/2012 | Uchida |
| 2012/0274783 | A1* | 11/2012 | Ko et al. ......................... 348/169 |
| 2012/0281235 | A1* | 11/2012 | Murata et al. ................. 356/479 |

FOREIGN PATENT DOCUMENTS

| CN | 1618394 A | 5/2005 |
| CN | 102264282 A | 11/2011 |
| EP | 1 316 287 A2 | 6/2003 |

(Continued)

OTHER PUBLICATIONS

Ip et al. "Fundus Bsed Eye Tracker for Optical Coherence Tomography." 26th Annual International Conference of the IEEE Engineering in Medicine and Biology Society, Sep. 2004, p. 1505-1508.*

(Continued)

*Primary Examiner* — Jon Chang
(74) *Attorney, Agent, or Firm* — Fitzpatrick, Cella, Harper & Scinto

(57) ABSTRACT

An optical coherence tomographic apparatus includes a unit configured to perform tracking of an eye to be examined based on a plurality of images of the eye which are obtained at different times, and a control unit configured to control the unit which performs the tracking in a case where a plurality of tomographic images of the eye are obtained.

37 Claims, 11 Drawing Sheets

(56) References Cited

FOREIGN PATENT DOCUMENTS

| | | |
|---|---|---|
| JP | 2001-178678 A | 7/2001 |
| JP | 2008-029467 A | 2/2008 |
| JP | 2008-154725 A | 7/2008 |
| JP | 4354601 B2 | 10/2009 |
| JP | 2011-115507 A | 6/2011 |
| WO | 2010/063416 A1 | 6/2010 |
| WO | 2012/130976 A1 | 10/2012 |

OTHER PUBLICATIONS

May 14, 2013 European Official Action in European Patent Application No. 13152654.3.

Jul. 30, 2014 Chinese Official Action in Chinese Patent Appln. No. 201310032544.1.

* cited by examiner

F I G. 1
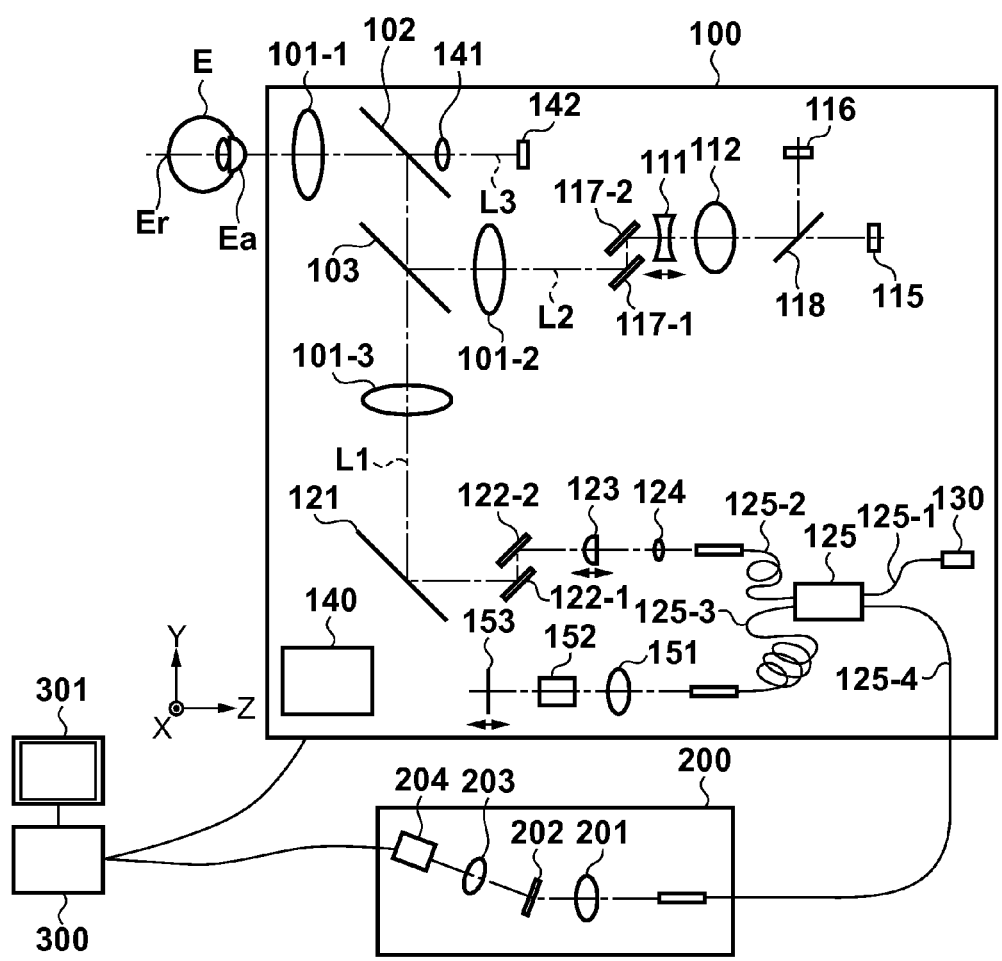

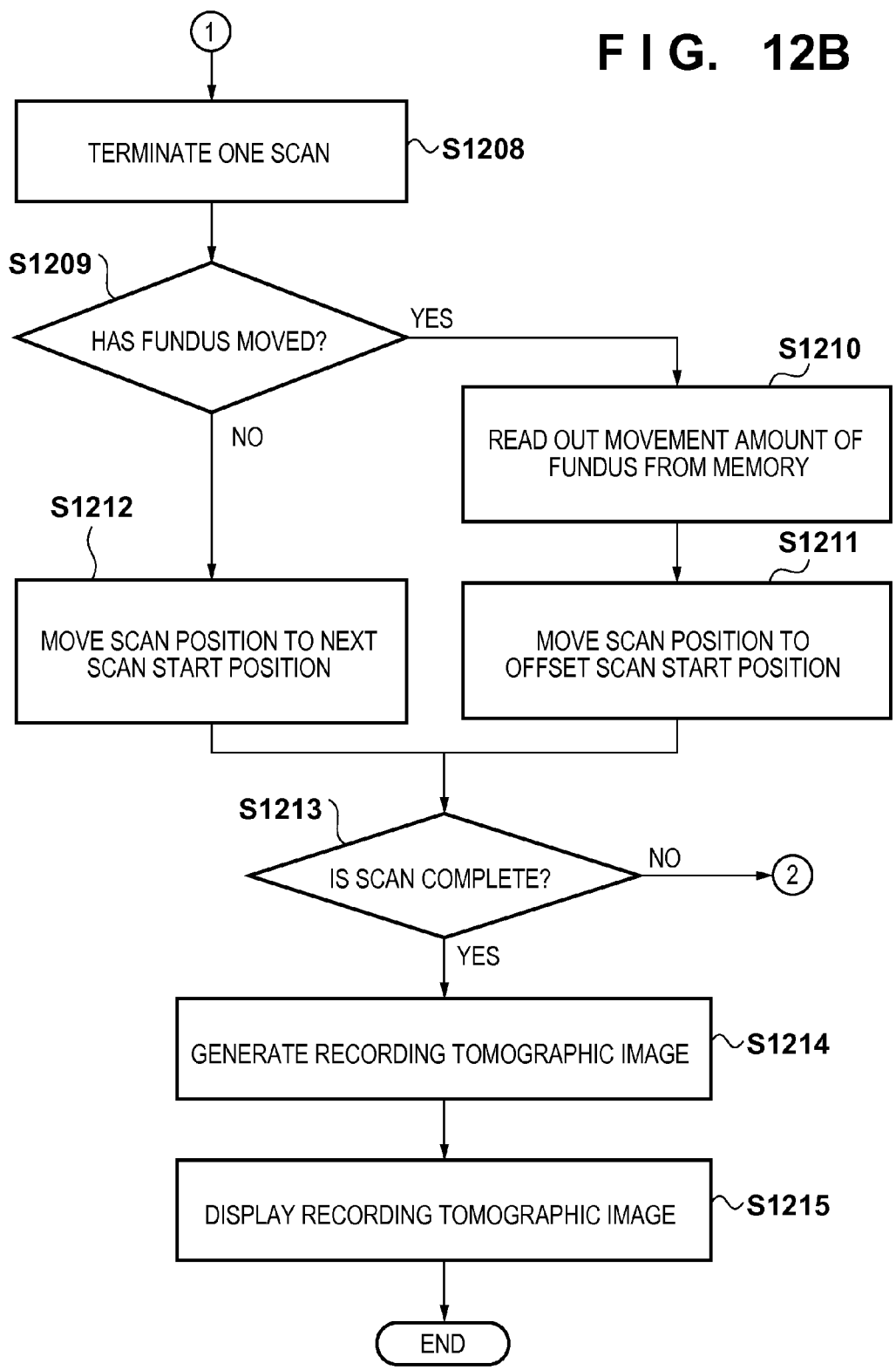

OPTICAL COHERENCE TOMOGRAPHIC APPARATUS, CONTROL METHOD FOR OPTICAL COHERENCE TOMOGRAPHIC APPARATUS AND STORAGE MEDIUM

BACKGROUND OF THE INVENTION

1. Field of the Invention

The present invention relates to an optical coherence tomographic apparatus, a control method for the optical coherence tomographic apparatus, and a storage medium.

2. Description of the Related Art

Currently, optical coherence tomographic apparatuses based on OCT (Optical Coherence Tomography) using multiwavelength light wave coherence are known. For example, such apparatuses are used to obtain organ information with an endoscope and retina information in an ophthalmic apparatus. The application field of these apparatuses to the human bodies has become more and more broad. An optical coherence tomographic apparatus applied to the eyes is becoming indispensable in outpatient clinics specialized in retinas as an ophthalmic apparatus.

Such an optical coherence tomographic apparatus is an apparatus which performs measurement by irradiating a sample with measurement light which is low-coherent light, and by using backscattered light from the sample for an interference system. Irradiating one point on a sample with measurement light can obtain image information in the depth direction at the point on the sample. In addition, performing measurement while scanning measurement light on a sample can obtain a tomographic image of the sample. When applying this apparatus to the fundus, it is possible to capture a tomographic image of the fundus of the eye to be examined at high resolution by scanning measurement light on the fundus of the eye. For this reason, these apparatuses are widely used for ophthalmic diagnosis of the retinas and the like.

Optical coherence tomographic apparatuses generally use an imaging method of obtaining a plurality of tomographic images by reciprocally scanning on the fundus as a measurement target in the horizontal or vertical direction. For example, it is possible to obtain one high-quality fundus tomographic image by obtaining a plurality of fundus tomographic images of the same region by performing scanning on the same region on the fundus a plurality of times and performing averaging processing of the obtained images. It is also possible to obtain a three-dimensional image of the fundus by performing scanning a plurality of times while translating the scan position. When, however, performing scanning a plurality of times in this manner, it takes a certain period of time to complete the imaging operation. For this reason, the eye may move during the operation.

In contrast to this, according to the ophthalmic imaging apparatus disclosed in Japanese Patent Laid-Open No. 2008-29467, there is disclosed a method (fundus tracking) of sequentially capturing front images of the eye to be examined, detecting the movement of the eye by using a plurality of obtained front images, and correcting the scan position in accordance with the detected movement of the eye. As described above, it is important for the optical coherence tomographic apparatus to perform the processing of reducing the influence of the movement of the eye.

On the other hand, it is important for the optical coherence tomographic apparatus to keep the positional relationship between the eye to be examined and the apparatus main body constant. In order to obtain a high-quality fundus tomographic image, it is necessary to match the imaging optical axis of the optical coherence tomographic apparatus with the pupil position of the eye to be examined and to adjust the relative positions of the imaging optical system and the eye to be examined so as to make imaging light fall within the pupil.

In contrast to this, according to the ophthalmic apparatus disclosed in Japanese Patent No. 4354601, there is disclosed an automatic alignment mechanism for automatically adjusting the relative positional relationship between the eye to be examined and an optical storage portion.

SUMMARY OF THE INVENTION

It is an object of the present invention to obtain a tomographic image with reduced distortion caused by the movement of the eye to be examined even when performing tracking in accordance with the movement of the eye.

According to one aspect of the present invention, there is provided an optical coherence tomographic apparatus including an optical coherence tomographic apparatus comprising: an image obtaining unit configured to obtain a plurality of images of an eye to be examined at different times; a unit configured to perform tracking of the eye based on the plurality of images; a tomographic image obtaining unit configured to obtain a plurality of tomographic images of the eye based on interfering light obtained by interference between return light from the eye irradiated with measurement light and reference light corresponding to the measurement light; and a control unit configured to control the unit which performs the tracking in a case where the plurality of tomographic images are obtained.

Further features of the present invention will be apparent from the following description of exemplary embodiments with reference to the attached drawings.

BRIEF DESCRIPTION OF THE DRAWINGS

FIG. 1 is a view showing an example of the arrangement of an optical coherence tomographic apparatus;

FIGS. 12A and 12B are flowcharts showing an example of fundus tracking control.

DESCRIPTION OF THE EMBODIMENTS

Figure 2:
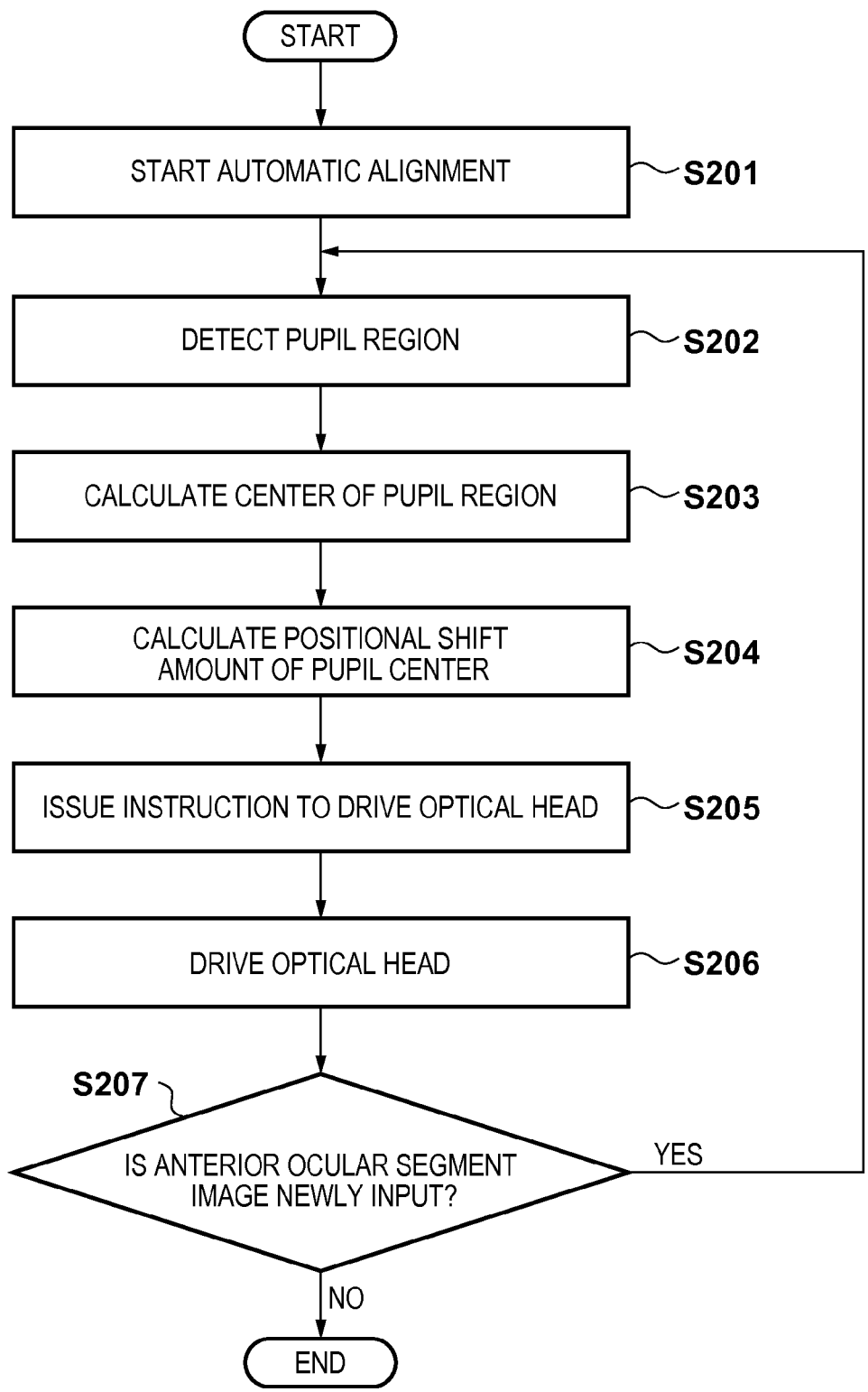
FIG. 2 is a flowchart showing an example of automatic alignment operation.

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

It is an object of the present invention to obtain a tomographic image with reduced distortion caused by the movement of the eye to be examined even when performing tracking in accordance with the movement of the eye.

A tomographic image may distort at the time of the above scan position correction (fundus tracking) or automatic alignment during scanning of measurement light on the eye to be examined to capture a tomographic image of the eye.

When, for example, automatic alignment is activated during capturing of a tomographic image, the retina on the tomographic image may tilt or vertically move due to the decentering of the imaging optical axis which is caused by automatic alignment. When, in particular, the apparatus performs scanning a plurality of times to obtain a plurality of tomographic images, the retina on a given tomographic image may be located horizontally while the retina may tilt on another tomographic image. When the apparatus has captured a plurality of tomographic images with different tilts, the differences in tilt between the respective tomographic images appear as the distortion of the retina shape on the three-dimensional image generated from the plurality of tomographic images.

When fundus tracking is activated during capturing of a tomographic image, a tomographic image may also distort due to the correction of the scan position by fundus tracking. If the intervals of correction by fundus tracking are shorter than the time (A-scan obtaining time) taken to obtain information in the depth direction at one point on the eye to be examined, since the scan position is properly corrected at each scan point to obtain one tomographic image, no distortion occurs in the tomographic image. It is however difficult to make the intervals of correction by fundus tracking shorter than the A-scan obtaining time. For example, the apparatus often uses front images of the fundus in fundus tracking, and it is difficult to make the correction intervals shorter than the intervals of obtaining front images. In general, the intervals of obtaining front images are about several ten ms, which are longer than the A-scan obtaining intervals (several ten μs in general). This makes it difficult to perform correction by fundus tracking for each point in scanning on the eye to be examined. For this reason, the apparatus performs this correction at predetermined intervals for each scan range of a certain size. Assume that the apparatus has corrected the scan position at predetermined intervals. In this case, the apparatus corrects the movement of the eye detected during a predetermined interval at a time. As a result, the scan position abruptly changes at predetermined intervals in scanning on the eye to be examined. Abrupt changes in scan position appear as slice displacement (distortion) at predetermined intervals on the captured tomographic image.

The above distortion on the tomographic image hinders the doctor from performing image diagnosis. In addition, the doctor may erroneously recognize the distortion on the tomographic image as a lesion. This may lead to misdiagnosis. Furthermore, distortion on a tomographic image may adversely affect an automatic recognition function for retinal layer boundaries of the optical coherence tomographic apparatus. Erroneously recognizing retinal layer boundaries will display the measurement value of a retinal layer thickness and the like based on the erroneous recognition result. This may lead to misdiagnosis.

When obtaining a plurality of tomographic images of the eye to be examined, it is preferable to control a unit for tracking the eye. This makes it possible to obtain a tomographic image with reduced distortion caused by the movement of the eye. For example, the unit for tracking the eye to be examined preferably operates such that after one of a plurality of tomographic images is obtained, the obtaining position of the next tomographic image is corrected by the time the next tomographic image is obtained. This operation will be concretely described below in each embodiment.

(First Embodiment)

<Schematic Arrangement of Optical Coherence Tomographic Apparatus>

The schematic arrangement of an optical coherence tomographic apparatus according to the first embodiment will be described with reference to FIG. 1. The optical coherence tomographic apparatus obtains a tomographic image of the eye to be examined based on the interfering light obtained by interference between return light from the eye irradiated with measurement light through a scanning unit and reference light corresponding to the measurement light. The optical coherence tomographic apparatus includes an optical head unit 100, a spectrometer 200, and a control unit 300. The arrangements of the optical head unit 100, spectrometer 200, and control unit 300 will be sequentially described below.

<Arrangements of Optical Head Unit 100 and Spectrometer 200>

The optical head unit 100 is formed from a measurement optical system for capturing two-dimensional images and tomographic images of an an anterior ocular segment Ea of eye E to be examined, and a fundus Er of the eye. The interior of the optical head unit 100 will be described below. An objective lens 101-1 is disposed to face the eye E. On the optical axis of this lens, a first dichroic mirror 102 and a second dichroic mirror 103, which function as optical path separation units, separate the optical path. That is, they separate the optical path for each wavelength band into a measurement optical path L1 of an OCT optical system, a fundus observation optical path/fixation lamp optical path L2, and an anterior eye observation optical path L3.

A third dichroic mirror 118 further branches, for each wavelength band, the optical path L2 into optical paths to an APD (avalanche photodiode) 115 for fundus observation and to a fixation lamp 116. In this case, reference numerals 101-2, 111, and 112 denote lenses. A motor (not shown) for focus adjustment for a fixation lamp and fundus observation drives the lens 111. The APD 115 has sensitivity near the wavelength of fundus observation illumination light (not shown), more specifically, 780 nm. On the other hand, the fixation lamp 116 generates visible light to urge the object to fix the vision.

An X scanner 117-1 (for the main scanning direction) for scanning the light emitted from a fundus observation illumination light source (not shown) on the fundus Er of the eye E and a Y scanner 117-2 (for the sub-scanning direction intersecting the main scanning direction) are disposed on the optical path L2. The lens 101-2 is disposed such that its focal position is located near the central position between the X scanner 117-1 and the Y scanner 117-2. The X scanner 117-1 is formed from a resonance mirror but may be formed from a polygon mirror. A position near the central position between the X scanner 117-1 and the Y scanner 117-2 is optically conjugate to the position of the pupil of the eye E. The APD (avalanche photodiode) 115 is a single detector, which detects light scattered/reflected by the fundus Er. The third dichroic mirror 118 is a prism on which a perforated mirror or hollow mirror is deposited, and separates illumination light and return light from the fundus Er.

A lens 141 and an infrared CCD 142 for anterior eye observation are disposed on the optical path L3. The infrared CCD 142 has sensitivity near the wavelength of anterior eye observation illumination light (not shown), more specifically, 970 nm. The optical path L1 forms an OCT optical system, as described above, and is used to capture a tomographic image of the fundus Er of the eye. More specifically, this optical path is used to obtain an interfering signal for forming a tomographic image.

A lens 101-3, a mirror 121, and an X scanner 122-1 and Y scanner 122-2 which function as scanning units to scan light on the fundus Er of the eye are disposed on the optical path L1. In addition, the X scanner 122-1 and the Y scanner 122-2 are disposed such that a position near the central position between the X scanner 122-1 and the Y scanner 122-2 becomes the focal position of the lens 101-3. Furthermore, a position near the central position between the X scanner 122-1 and the Y scanner 122-2 is optically conjugate to the position of the pupil of the eye E. According to this arrangement, an optical path with a scanning unit serving as an object point becomes almost parallel between the lens 101-1 and the lens 101-3. This can make the incident angle of light on the first dichroic mirror 102 coincide with that on the second dichroic mirror 103, even when the X scanner 122-1 and the Y scanner 122-2 perform scanning.

A measurement light source 130 is a light source for making measurement light enter a measurement optical path. In this embodiment, the measurement light source 130 is disposed on a fiber end and optically conjugate to the fundus Er of the eye E. Reference numerals 123 and 124 denote lenses. Of the lenses 123 and 124, the lens 123 is driven by a motor (not shown) to perform focus adjustment. Focus adjustment is performed by adjusting the light emitted from the measurement light source 130 on the fiber end so as to focus the light on the fundus Er. The lens 123 functioning as a focus adjustment unit is disposed between the measurement light source 130 and the X scanner 122-1 and Y scanner 122-2 which function as scanning units. This makes it unnecessary to use a lens larger than the lens 101-3 or move an optical fiber 125-2.

This focus adjustment makes it possible to form an image of the measurement light source 130 on the fundus Er of the eye E and to efficiently return return light from the fundus Er of the eye E to the fiber 125-2 through the measurement light source 130.

Note that the optical path between the X scanner 122-1 and the Y scanner 122-2 in FIG. 1 runs within the drawing surface. In practice, however, this optical path runs in a direction perpendicular to the drawing surface. The optical head unit 100 further includes a head driving unit 140. The head driving unit 140 is constituted by three motors (not shown) and is configured to move the optical head unit 100 in the three-dimensional (X, Y, Z) directions relative to the eye E. This makes it possible to align the optical head unit 100 to the eye E.

The optical path from the measurement light source 130 and the arrangements of the reference optical system and spectrometer 200 will be described next. The measurement light source 130, an optical coupler 125, optical fibers 125-1 to 125-4, a lens 151, a dispersion-compensating glass 152, a mirror 153, and the spectrometer 200 constitute a Michelson interferometer. The optical fibers 125-1 to 125-4 are single-mode optical fibers, which are connected to the optical coupler 125 so as to be integrated.

The light emitted from the measurement light source 130 is divided into measurement light which propagates to the optical fiber 125-2 through the optical fiber 125-1 and the optical coupler 125 and reference light which propagates to the optical fiber 125-3 through the optical fiber 125-1 and the optical coupler 125. The measurement light enters the fundus Er of the eye E as an observation target through the above OCT optical system optical path and reaches the optical coupler 125 through the same optical path by reflection and scattering by the retina.

On the other hand, reference light reaches and is reflected by the mirror 153 through the optical fiber 125-3, the lens 151, and the dispersion-compensating glass 152 inserted to match the dispersion of measurement light with that of reference light. The reference light returns along the same path and reaches the optical coupler 125. The optical coupler 125 combines the measurement light with the reference light to form interfering light. When the optical path length of measurement light almost coincides with that of reference light, interference occurs. A motor and driving mechanism (not shown) hold the mirror 153 so as to adjust its position in the optical axis direction, thereby matching the optical path length of measurement light, which changes depending on the eye E, with that of reference light. Interfering light is guided to the spectrometer 200 through the optical fiber 125-4.

The spectrometer 200 includes a lens 201, a diffraction grating 202, a lens 203, and a line sensor 204. The interfering light emerging from the optical fiber 125-4 is made almost parallel through the lens 201, and then spectroscoped by the diffraction grating 202. The lens 203 forms the light into an image on the line sensor 204.

An arrangement around the light source 130 will be described next. The light source 130 is an SLD (Super Luminescent Diode) which is a typical low-coherent light source. The central wavelength is 855 nm, and the wavelength bandwidth is about 100 nm. In this case, the bandwidth is an important parameter which influences the resolution of an obtained tomographic image in the optical axis direction. In addition, an SLD is selected as a light source in this case. However, ASE (Amplified Spontaneous Emission) or the like may be used as long as it can emit low-coherent light. In consideration of measurement of the eye to be examined, the wavelength of infrared light is suitable as the central wavelength to be set. In addition, the central wavelength influences the resolution of an obtained tomographic image in the horizontal direction, and hence is preferably as short as possible. For the two reasons, the central wavelength is set to 855 nm.

Although this embodiment uses a Michelson interferometer as an interferometer, a Mach-Zehnder interferometer may be used. It is preferable to use a Mach-Zehnder interferometer when the light amount difference between measurement light and reference light is large, and a Michelson interferometer when the light amount difference is relatively small.

<Arrangement of Control Unit 300>

The control unit 300 is connected to the respective units of the optical head unit 100 and spectrometer 200. More specifically, the control unit 300 is connected to the infrared CCD 142 in the optical head unit 100 and is configured to generate an observation image of the anterior ocular segment Ea of the eye E. The control unit 300 is also connected to the APD 115 in the optical head unit 100 and is configured to generate an observation image of the fundus Er of the eye E. In addition, the control unit 300 is connected to the head driving unit 140 in the optical head unit 100 and is configured to three-dimensionally drive the optical head unit 100 relative to the eye E.

The control unit 300 is connected to the line sensor 204 of the spectrometer 200. This makes it possible to obtain the measurement signal wavelength-decomposed by the spectrometer 200, and can generate a tomographic image of the eye E based on the measurement signal.

A monitor 301 connected to the control unit 300 can display the generated anterior ocular segment observation image, fundus observation image, and tomographic image of the eye E.

<Alignment Method for Eye E>

An alignment method for eye E which uses the optical coherence tomographic apparatus according to this embodiment will be described next with reference to the flowchart of FIG. 2. Prior to imaging operation, first of all, the examiner lets an object sit in front of the apparatus.

In step S201, the control unit 300 starts automatic alignment upon accepting switch operation (not shown) by the examiner. In step S202, the control unit 300 functions as an anterior ocular segment image obtaining unit, and periodically obtains and analyzes an anterior ocular segment image from the infrared CCD 142 at the start of automatic alignment. More specifically, the control unit 300 detects a pupil region in an input anterior ocular segment image.

In step S203, the control unit 300 calculates the central position of the detected pupil region. In step S204, the control unit 300 functions as a positional shift amount calculation unit and calculates the central position of the detected pupil region and a displacement amount (positional shift amount) from the central position of the anterior ocular segment image. The optical coherence tomographic apparatus of this embodiment is configured to match the center of an anterior ocular segment image with the optical axis of the objective lens 101-1. The displacement amount calculated in step S204 represents the positional shift amount between the eye E and the measurement optical axis.

In step S205, the control unit 300 instructs the head driving unit 140 to move the optical head unit 100 in accordance with the positional shift amount calculated in step S204. In step S206, the head driving unit 140 drives the three motors (not shown) to move the position of the optical head unit 100 in the three-dimensional (X, Y, Z) directions relative to the eye E. As a result of movement, the position of the optical axis of the objective lens 101-1 mounted on the optical head unit 100 is corrected to approach the central position of the pupil of the anterior ocular segment Ea of the eye E.

In step S207, the control unit 300 determines, after the movement of the optical head unit 100, whether an anterior ocular segment image is newly input from the infrared CCD 142. If the control unit 300 determines that an anterior ocular segment image is newly input (YES in step S207), the process returns to step S202. If the control unit 300 determines that no anterior ocular segment image is newly input (NO in step S207), the apparatus terminates the processing.

With this series of automatic alignment operation, the optical axis position of the objective lens 101-1 always moves so as to track the central position of the pupil of the anterior ocular segment Ea of the eye E. Even if the line-of-sight direction of the eye E changes, this automatic alignment operation makes the optical axis of the objective lens 101-1 track (anterior eye tracking) the pupil center of the anterior ocular segment Ea after the change in line of sight. This makes it possible to irradiate the fundus Er with the measurement light beam emitted from the measurement light source 130 without being blocked by the pupil, thereby stably capturing tomographic images.

In order to record a tomographic image of the fundus Er of the eye E, the apparatus continues this series of automatic alignment operation until the start of scanning of measurement light on the fundus Er of the eye E.

Although this embodiment performs automatic alignment of the optical system relative to the eye to be examined based on the anterior ocular segment image captured by the infrared CCD, it is possible to execute this operation by using other techniques. For example, projecting an index for alignment on the anterior ocular segment of the eye and detecting reflected light can perform automatic alignment in the three-dimensional (X, Y, Z) directions.

<Fundus Tracking Method>

Figure 3:
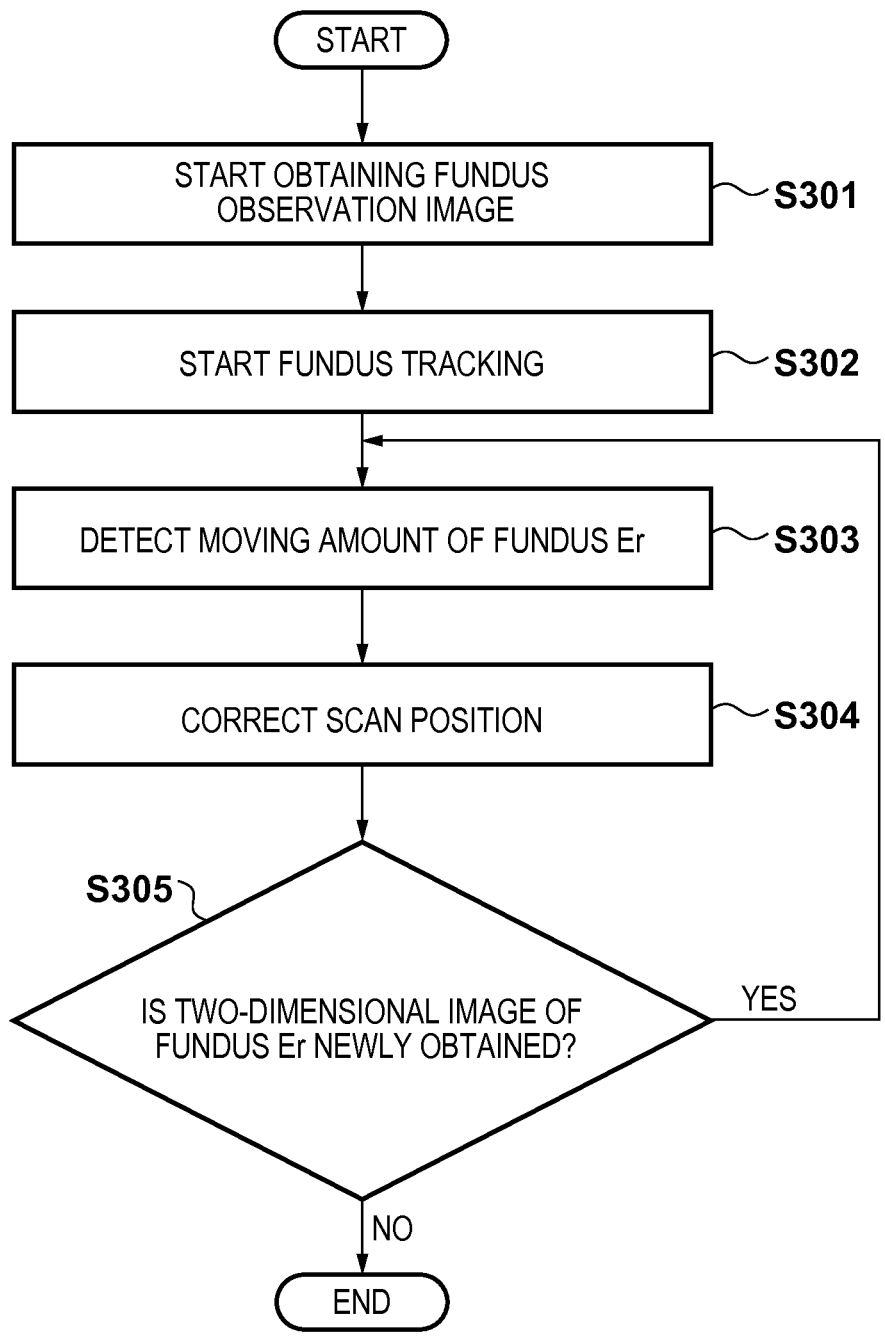
FIG. 3 is a flowchart showing an example of fundus tracking operation.

A fundus tracking method of correcting the shift of the measurement light irradiation position caused accompanying the movement of the eye E when the fundus Er of the eye E is irradiated with measurement light for the observation of the state of the eye E will be described next with reference to the flowchart of FIG. 3.

In step S301, the control unit 300 starts obtaining a two-dimensional observation image of the fundus Er through the optical path L2 after the start of the above automatic alignment operation. More specifically, the control unit 300 starts obtaining reflected light from the fundus Er which is input from the APD 115. The X scanner 117-1 and the Y scanner 117-2 two-dimensionally and continuously scan reflected light from the fundus Er on the fundus Er. Periodically synthesizing reflected light input from the APD 115 can periodically obtain an observation image of the fundus Er.

In step S302, the control unit 300 starts fundus tracking operation based on a periodically obtained fundus observation image. In step S303, the control unit 300 calculates the movement amount of the fundus Er by using two fundus observation images including a previously obtained fundus observation image and a currently obtained fundus observation image. More specifically, the control unit 300 calculates the movement amount of the fundus Er in the two-dimensional (X, Y) directions by calculating the displacement amount of a region of interest on the fundus observation image in the two-dimensional (X, Y) directions.

In step S304, the control unit 300 controls the X scanner 122-1 and the Y scanner 122-2 in accordance with the calculated movement amount of the fundus Er, thereby correcting the scan position so as to always irradiate the same region on the fundus Er with measurement light along the optical path L1.

In step S305, the control unit 300 determines whether a two-dimensional observation image of the fundus Er has been newly obtained. If the control unit 300 determines that a two-dimensional observation image of the fundus Er has been newly obtained (YES in step S305), the process returns to step S303. If the control unit 300 determines that no two-dimensional observation image of the fundus Er has been newly obtained (NO in step S305), the apparatus terminates the processing.

With this series of fundus tracking operation, the measurement light applied from the measurement light source 130 onto the fundus Er always moves so as to track the movement of the fundus Er of the eye to be examined. This allows to stably capture tomographic images. The apparatus continues this series of fundus tracking operation until the end of examination on the eye E.

Although this embodiment performs fundus tracking by using fundus observation images obtained by a point scanning type SLO, it is possible to execute this operation by using other techniques. For example, it is possible to perform fundus tracking by using the two-dimensional fundus observation images obtained by a combination of infrared light which can irradiate the fundus in a wide range and an infrared CCD.

In addition, it is possible to perform fundus tracking by using reflected light obtained by projecting an arbitrary pattern formed from a light source onto the fundus.

<Method of Capturing Tomographic Image>

A method of capturing a tomographic image by using the optical coherence tomographic apparatus of this embodiment will be described next.

The examiner starts imaging operation by operating a switch (not shown) on the control unit 300. In accordance with an instruction to start imaging, the control unit 300 starts generating a tomographic image for recording based on the interfering light periodically output from the line sensor 204.

In this case, the interfering light output from the line sensor 204 is a signal for each frequency spectroscoped by the diffraction grating 202. The control unit 300 performs FFT (Fast Fourier Transform) processing of a signal from the line sensor 204 to generate information in the depth direction at a given point on the fundus Er. The generation of information in the depth direction at a given point on the fundus Er will be referred to as A-scan.

It is possible to arbitrarily scan, on the fundus Er, the measurement light applied on the fundus Er by driving/controlling at least one of the X scanner 122-1 and the Y scanner 122-2. It is possible to scan measurement light on the eye to be examined by using the X scanner 122-1 and the Y scanner 122-2.

The control unit 300 generates a tomographic image on an arbitrary locus on the fundus Er by combining a series of a plurality of A-scan images, obtained during one scan on this arbitrary locus, on one two-dimensional image.

In addition, the control unit 300 repeats scanning on the above arbitrary locus a plurality of times by driving/controlling at least one of the X scanner 122-1 and the Y scanner 122-2. Repeating scanning on the same locus a plurality of times can obtain a plurality of tomographic images on the arbitrary locus on the fundus Er. For example, the control unit 300 repeatedly executes scanning in the X direction by driving only the X scanner 122-1 to generate a plurality of tomographic images on the same scanning line on the fundus Er. The control unit 300 can also generate a plurality of tomographic images on the same circle on the fundus Er by repeatedly executing a circular scan by simultaneously driving the X scanner 122-1 and the Y scanner 122-2. The control unit 300 generates a high-quality tomographic image by performing averaging processing of the plurality of tomographic images, and displays the image on the monitor 301.

On the other hand, the control unit 300 can perform scanning on the above arbitrary locus a plurality of times while shifting the scan position in the X and Y directions by driving/controlling at least one of the X scanner 122-1 and the Y scanner 122-2. Performing scanning in the X direction at predetermined intervals a plurality of times while shifting the scan position in the Y direction will generate a plurality of tomographic images covering the overall rectangular region on the fundus Er. The control unit 300 generates the three-dimensional information of the fundus Er by combining the plurality of tomographic images, and displays the image on the monitor 301.

It is possible to arbitrarily switch the scan patterns by the X scanner 122-1 and the Y scanner 122-2 by pressing a scan pattern selection button (not shown).

<Automatic Alignment Control During Capturing of Tomographic Images>

When performing a plurality of scans like those described above to capture a plurality of tomographic images, the time required to perform these scans is longer than the time required to perform one scan. Assume that the optical coherence tomographic apparatus according to this embodiment can repeat a 10-mm scan on the fundus Er in the X direction 128 times while shifting the scan position 0.078 mm at a time in the Y direction. Performing this scan 128 times can obtain 128 tomographic images and generate three-dimensional information in the range of 10 mm×10 mm on the fundus Er. In the optical coherence tomographic apparatus according to this embodiment, one tomographic image is constituted by a total of 1024 A-scan images. The time required to perform one A-scan is 14.3 µs. Therefore, it requires 1024×14.3 µs=14.6 ms to obtain one tomographic image, and hence it requires 14.6 ms/image×128=1.87 sec to obtain all 128 tomographic images.

Human eye movements can be classified into three types (saccade, drift, and tremolo). These eye movements are one type of involuntary movement, and it is difficult to completely suppress them even if, for example, an object fixes his/her eye on a fixation lamp or the like. In addition, the occurrence period of such movement is shorter than an imaging period of 1.87 sec, and such eye movement often occurs a plurality of times while the apparatus performs all 128 scans.

Figure 4:
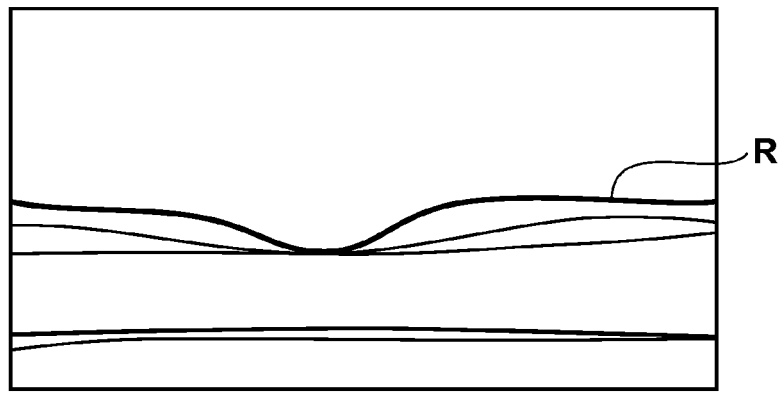
FIG. 4 is a view showing an example of a tomographic image captured in a proper alignment state.
Figure 5:
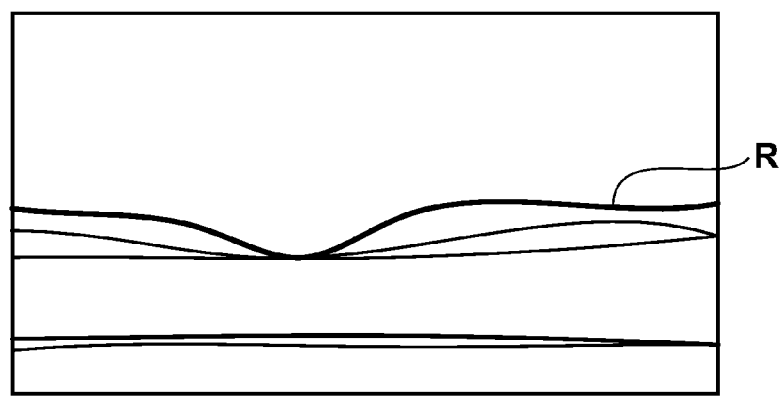
FIG. 5 is a view showing an example of a tomographic image captured in a state in which eye movement has occurred.

However, changes in pupil position due to these eye movements do not have much influence on captured tomographic images. FIG. 4 shows an example of a tomographic image captured while the pupil center of the anterior ocular segment Ea of the eye E coincides with the optical axis of the objective lens 101-1. FIG. 5 shows an example of a tomographic image captured while the pupil center shifts from the optical axis of the objective lens 101-1 by about 1 mm in the X direction. Although the tomographic image of the fundus Er shown in FIG. 5 is captured while a retina R shifts in the X direction relative to the tomographic image in FIG. 4, there is no great deformation in the tomographic image itself. In addition, such shift in the X direction can be corrected by fundus tracking described above.

Figure 6:
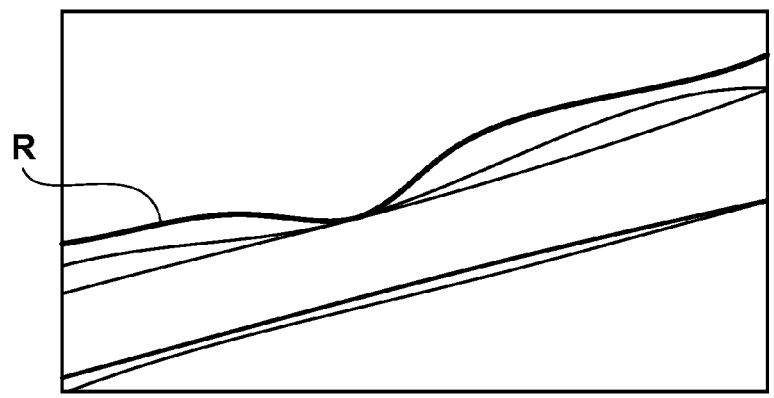
FIG. 6 is a view showing an example of a tomographic image captured during automatic alignment operation.
Figure 7:
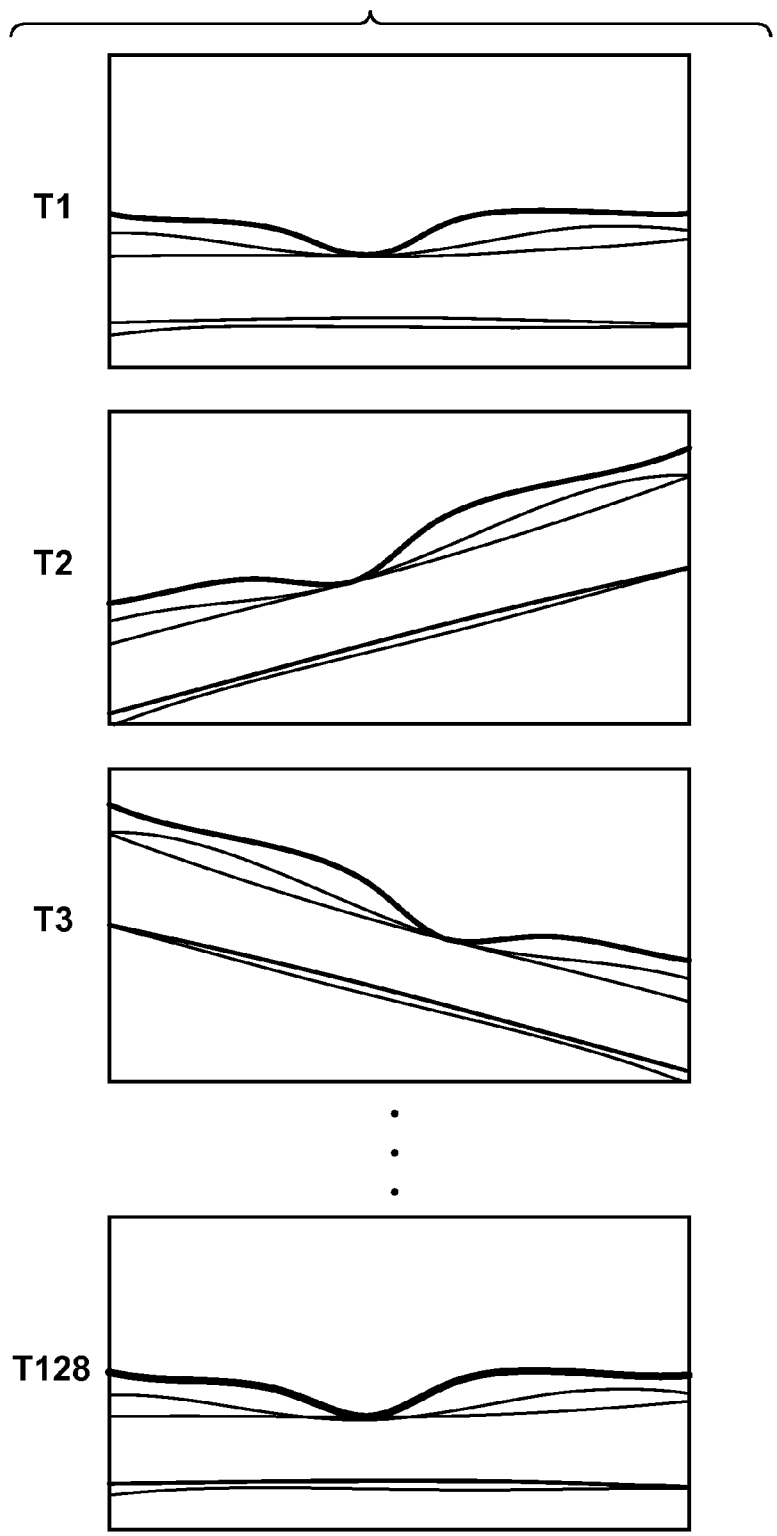
FIG. 7 is a view showing an example of a plurality of tomographic images captured during automatic alignment operation.
Figure 8:
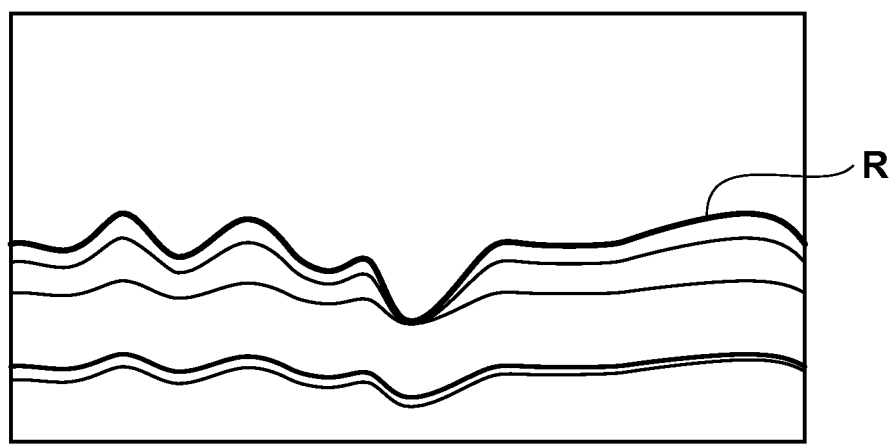
FIG. 8 is a view showing an example of the virtual tomographic image generated from a plurality of tomographic images in FIG. 7.

On the other hand, when automatic alignment is activated accompanying eye movement, a captured tomographic image is greatly influenced. FIG. 6 shows an example of a tomographic image captured while automatic alignment is activated for the state shown in FIG. 5 to match the pupil center with the optical axis of the objective lens 101-1. Obviously, as compared with the tomographic image in FIG. 4, there is not only a shift in the X direction but also a great tilt of the retina R. Fundus tracking cannot correct such tilt of the retina R. In addition, if automatic alignment is activated during all 128 scans, the tilt of the retina R greatly changes in the process of capturing 128 tomographic images, as shown in FIG. 7. Such changes in tilt raise a noticeable problem especially in the three-dimensional image generated by reconstructing a plurality of tomographic images. FIG. 8 shows an example of reconstructing the 128 tomographic images shown in FIG. 7 and displaying the resultant virtual tomographic image perpendicular to the main scanning direction. As is obvious, the shape of the retina R greatly changes in this virtual tomographic image. Changes in the tilt of the retina R may hinder the ophthalmologist who diagnoses an eye disease according to the form of the retina R from performing diagnosis, and lead to misdiagnosis.

The optical coherence tomographic apparatus according to this embodiment performs the processing of temporarily stopping the activation of automatic alignment during the execution of scanning for capturing a plurality of tomographic images. The operation of the apparatus will be described below with reference to the flowchart of FIG. 9. Prior to imaging operation, first of all, the examiner lets an object sit in front of the apparatus. Note that the control unit 300 drives/controls at least one of the X scanner 122-1 and the Y scanner 122-2 functioning as scanning units, and it is possible to switch between an observation scan for obtaining an observation tomographic image for the observation of the state of the eye to be examined and a recording scan for obtaining a recording tomographic image for recording the state of the eye.

In step S901, the control unit 300 starts automatic alignment upon accepting switch operation (not shown) by the examiner. In step S902, the control unit 300 starts obtaining an observation tomographic image of the fundus Er for the observation of an alignment state.

In step S903, the control unit 300 displays the obtained observation tomographic image on the monitor 301. The examiner can determine, by referring to the observation tomographic image displayed on the monitor 301, whether the alignment state is proper. If the examiner determines that the alignment state is proper, he/she issues an instruction to start capturing a tomographic image by operating a switch (not shown) of the control unit 300.

In step S904, the control unit 300 starts capturing a tomographic image to be recorded in response to the operation of the switch (not shown) by the examiner. In step S905, upon receiving the instruction to start imaging, the control unit 300 stops the activation of automatic alignment prior to imaging for recording.

In step S906, the control unit 300 starts scanning for the generation of a tomographic image for recording. More specifically, the control unit 300 executes scanning on an arbitrary locus a plurality of times by driving/controlling at least one of the X scanner 122-1 and the Y scanner 122-2.

In step S907, the control unit 300 resumes the activation of automatic alignment upon completion of all scans. In step S908, the control unit 300 generates a plurality of tomographic images corresponding to the plurality of scans. In step S909, the control unit 300 records the plurality of tomographic images generated in step S908 in a recording medium (not shown). With the above operation, the apparatus terminates the processing in the flowchart of FIG. 9.

In this embodiment, the apparatus stops automatic alignment immediately before the start of scanning for obtaining a tomographic image for recording. However, the apparatus may stop automatic alignment before the above timing. More specifically, the apparatus may stop automatic alignment at the time when determining that the automatic alignment almost matches the pupil position of the eye to be examined with the optical axis of the optical system.

Note that the apparatus may further include an acceptance unit which accepts a signal for obtaining a plurality of tomographic images, and may be configured to start the processing upon acceptance of the signal.

As described above, the optical coherence tomographic apparatus according to this embodiment can obtain an excellent tomographic image with little distortion by stopping the activation of automatic alignment at least when generating a tomographic image for recording.

<Fundus Tracking Control During Capturing of Tomographic Image>

Even when the apparatus performs fundus tracking during scanning for obtaining one tomographic image, there is a great influence on the captured tomographic image. As described above, the optical coherence tomographic apparatus according to this embodiment requires 14.6 ms to obtain one tomographic image. When, therefore, capturing a plurality of tomographic images, the apparatus performs scanning on the fundus Er a plurality of times at a period of about 14.6 ms. This period depends on the number of A-scans required for forming one tomographic image and the time required to obtain one A-scan. On the other hand, in the optical coherence tomographic apparatus according to this embodiment, the correction period of a scan position by fundus tracking is 33.3 ms. This period depends on the intervals of obtaining observation images of the fundus Er which are used to calculate a positional shift amount for correction.

Figure 10:
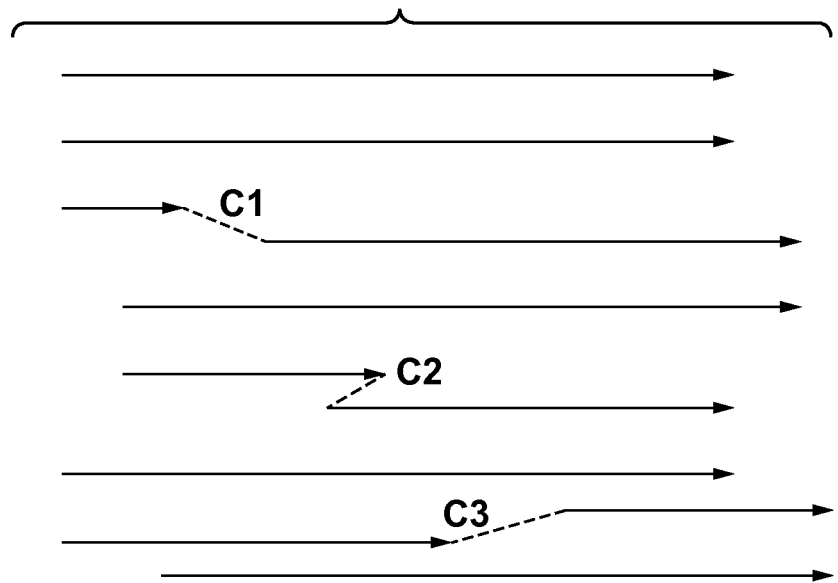
FIG. 10 is a view showing an example of a scan pattern without fundus tracking control.
Figure 11:
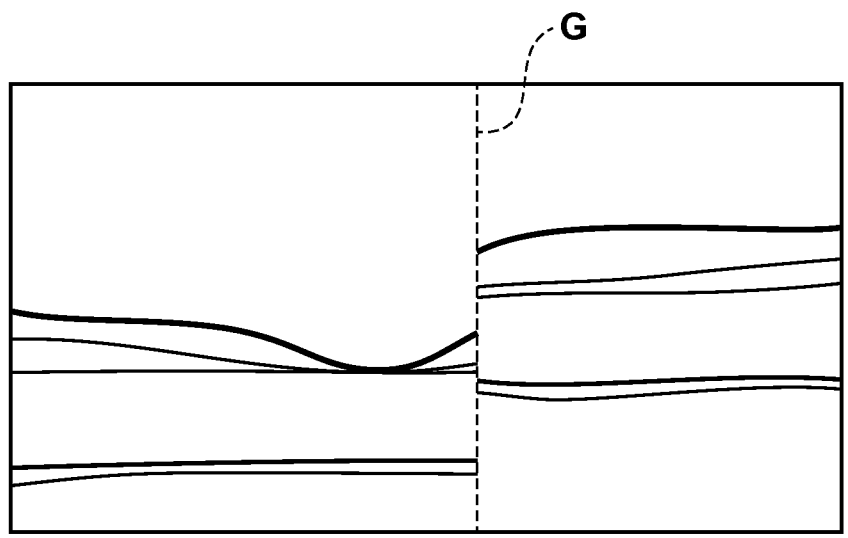
FIG. 11 is a view showing an example of the tomographic image obtained by the scan in FIG. 10.

As described above, if the intervals of obtaining tomographic images differ from the intervals of obtaining fundus observation images, the apparatus performs correction Ci (i=1 to 3) of the scan position by fundus tracking while scanning on the fundus Er to obtain one tomographic image, as shown in FIG. 10. In addition, in fundus tracking, although the intervals of correcting the scan position are long, the time required to actually perform correction is very short. Therefore, the correction of the scan position by fundus tracking is the operation of instantaneously correcting the position in accordance with all the eye movements performed within a correction interval. For this reason, if the apparatus corrects the scan position by fundus tracking while scanning on the fundus Er to obtain one tomographic image, a gap G between retinal layers appears, as shown in FIG. 11. The gap G between the retinal layers may hinder the ophthalmologist who diagnoses an eye disease according to the form of the retina from performing diagnosis, and lead to misdiagnosis.

In contrast to this, the optical coherence tomographic apparatus according to this embodiment performs correction of the scan position by fundus tracking in the interval between scans for obtaining each tomographic image while stopping the correction during each scan at the time of capturing a plurality of tomographic images. This operation will be described with reference to the flowcharts of FIGS. 12A and 12B. Prior to imaging operation, first of all, the examiner lets an object sit in front of the apparatus. Note that the control unit 300 drives/controls at least one of the X scanner 122-1 and the Y scanner 122-2 functioning as scanning units, and it is possible to switch and execute an observation scan for obtaining an observation tomographic image for the observation of the state of the eye to be examined and a recording scan for obtaining a recording tomographic image for recording the state of the eye.

In step S1201, the control unit 300 starts automatic alignment upon accepting switch operation (not shown) by the examiner. The apparatus then starts obtaining an observation tomographic image of the fundus Er to observe the alignment state. In step S1202, the control unit 300 displays the obtained observation tomographic image on the monitor 301. The examiner can determine, by referring to the observation tomographic image displayed on the monitor 301, whether the alignment state is proper.

In step S1203, the control unit 300 starts capturing a recording tomographic image when the examiner determines that the alignment state is proper, and the control unit 300 receives the operation of the switch (not shown) by the examiner. Note that the apparatus may correct the scan position based on fundus tracking in steps S1201 to S1203 for the adjustment of a coherence gate.

In step S1204, the control unit 300 starts one scan on an arbitrary locus by driving/controlling at least one of the X scanner 122-1 and the Y scanner 122-2 functioning as scanning units.

In step S1205, the control unit 300 functions as a fundus image obtaining unit, and determines whether a captured fundus image has been obtained. If the control unit 300 determines that a fundus image has been obtained (YES in step S1205), the process advances to step S1206. In contrast, if the control unit 300 determines that no fundus image has been obtained (NO in step S1205), the process advances to step S1208.

In step S1206, the control unit 300 functions as a movement amount calculation unit, and calculates the movement amount of the fundus Er from the already obtained fundus image and the newly obtained fundus image.

In step S1207, the control unit 300 stores, in a memory (not shown), information indicating that the movement of the fundus Er has been detected during one scan currently executed and information indicating the detected movement amount of the fundus Er. The process then advances to step S1208. In step S1208, the control unit 300 terminates the one scan.

In step S1209, the control unit 300 determines, according to the information stored in the memory (not shown), whether the movement of the fundus Er has been detected during the execution of the one scan. If the control unit 300 determines that the movement of the fundus Er has been detected (YES in step S1209), the process advances to step S1210. If the control unit 300 determines that no movement of the fundus Er has been detected (NO in step S1209), the process advances to step S1212.

In step S1210, the control unit 300 reads out the calculated movement amount from the memory (not shown). In step S1211, the control unit 300 calculates the next scan start position upon correcting the scan position by offsetting it by the movement amount of the fundus Er, and moves the next scan position to the offset scan start position.

In step S1212, the control unit 300 moves the scan position to the next scan start position by driving/controlling at least one of the X scanner 122-1 and the Y scanner 122-2 functioning as scanning units.

In step S1213, the control unit 300 determines whether a series of scans are all complete. If the control unit 300 determines the series of scans are complete (YES in step S1213), the process advances to step S1214. In contrast, if the control unit 300 determines that the series of scans are not complete (NO in step S1213), the process returns to step S1204 to repeat the series of fundus tracking operation.

In step S1214, the control unit 300 generates a plurality of recording tomographic images corresponding to a series of a plurality of scans. In step S1215, the control unit 300 displays the recording tomographic images generated in step S1214 on the monitor 301. With the above operation, the apparatus terminates the processing in the flowcharts of FIGS. 12A and 12B. In this manner, the apparatus stops the correction of the scan position during one scan, and corrects the scan position in the interval between one scan and the next scan.

An example of scanning will be described with reference to FIG. 13, in which the apparatus performs a plurality of scans on the fundus Er while performing fundus tracking in accordance with the flowcharts of FIGS. 12A and 12B. Let Di (i=1 to 3) be the timing when the movement of the fundus Er is detected, and Ci (i=1 to 3) be the timing when the scan position is corrected based on a calculated movement amount. As shown in FIG. 13, the apparatus delays the correction of the scan position accompanying the movement of the fundus Er detected at D1 to the start time of the next scan indicated by C1. Likewise, the apparatus delays the correction of the scan position accompanying the movement of the fundus Er detected at D2 and D3 to the time points indicated by C2 and C3, respectively. Performing control in this manner allows to continuously perform the respective scans on the fundus Er of the eye to be examined to the last without any interruption. This can reduce the possibility of the appearance of the gap G between the retinal layers like that shown in FIG. 11 on a captured recording tomographic image. Note that the gap G between the retinal layers will not likely appear on the tomographic image obtained by each of scans at D1, D2, and D3 at which the movement of the fundus Er has been detected, because no correction is performed on the scan position. However, since the fundus Er moves during scans, obtained tomographic images may slightly distort. Therefore, the apparatus may remove tomographic images obtained by the scans at D1, D2, and D3 or capture tomographic images again by performing the same scan at each scan position again. This makes it possible to obtain a tomographic image with less distortion.

Figure 9:
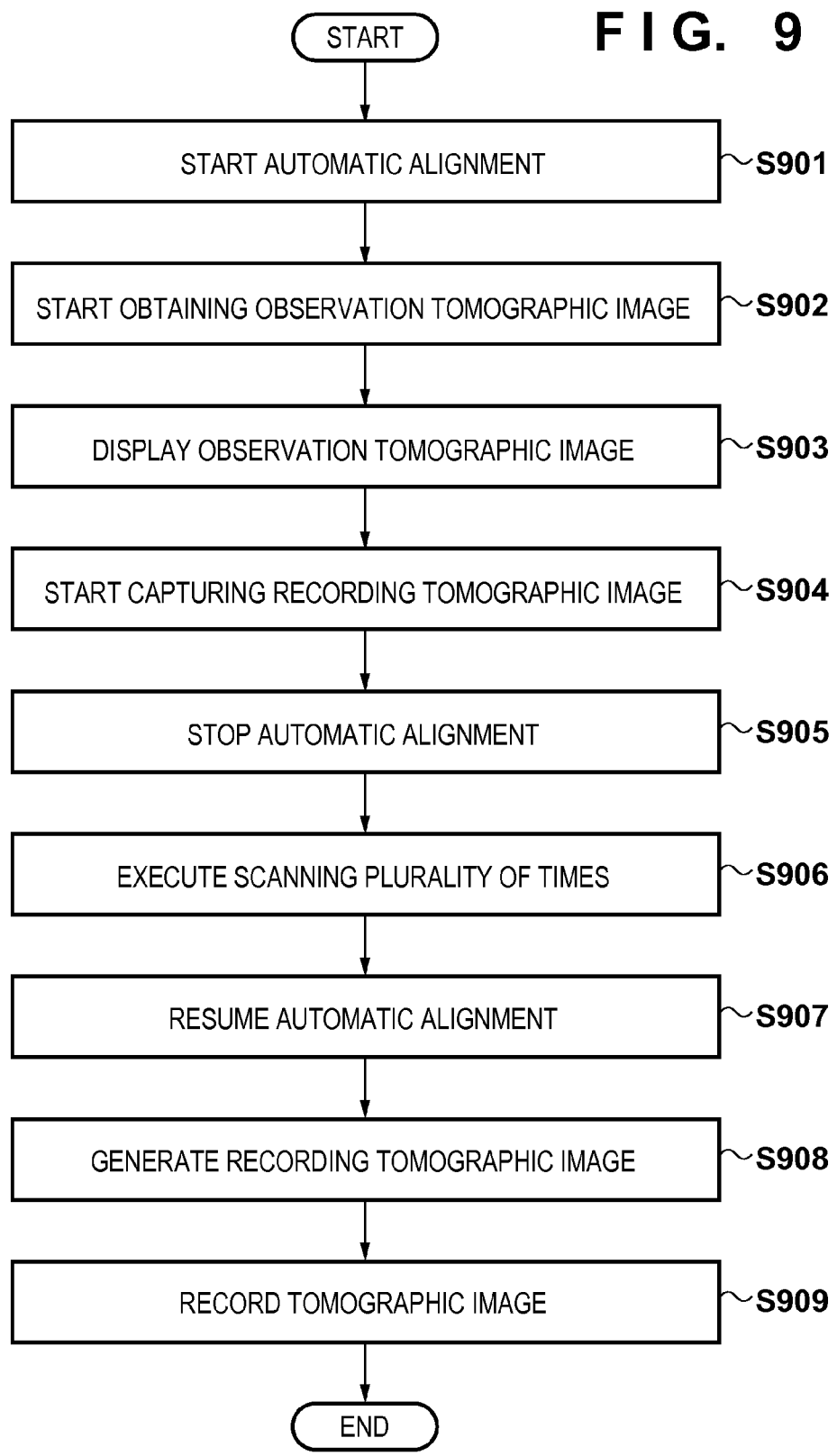
FIG. 9 is a flowchart showing an example of automatic alignment control.
Figure 12A:
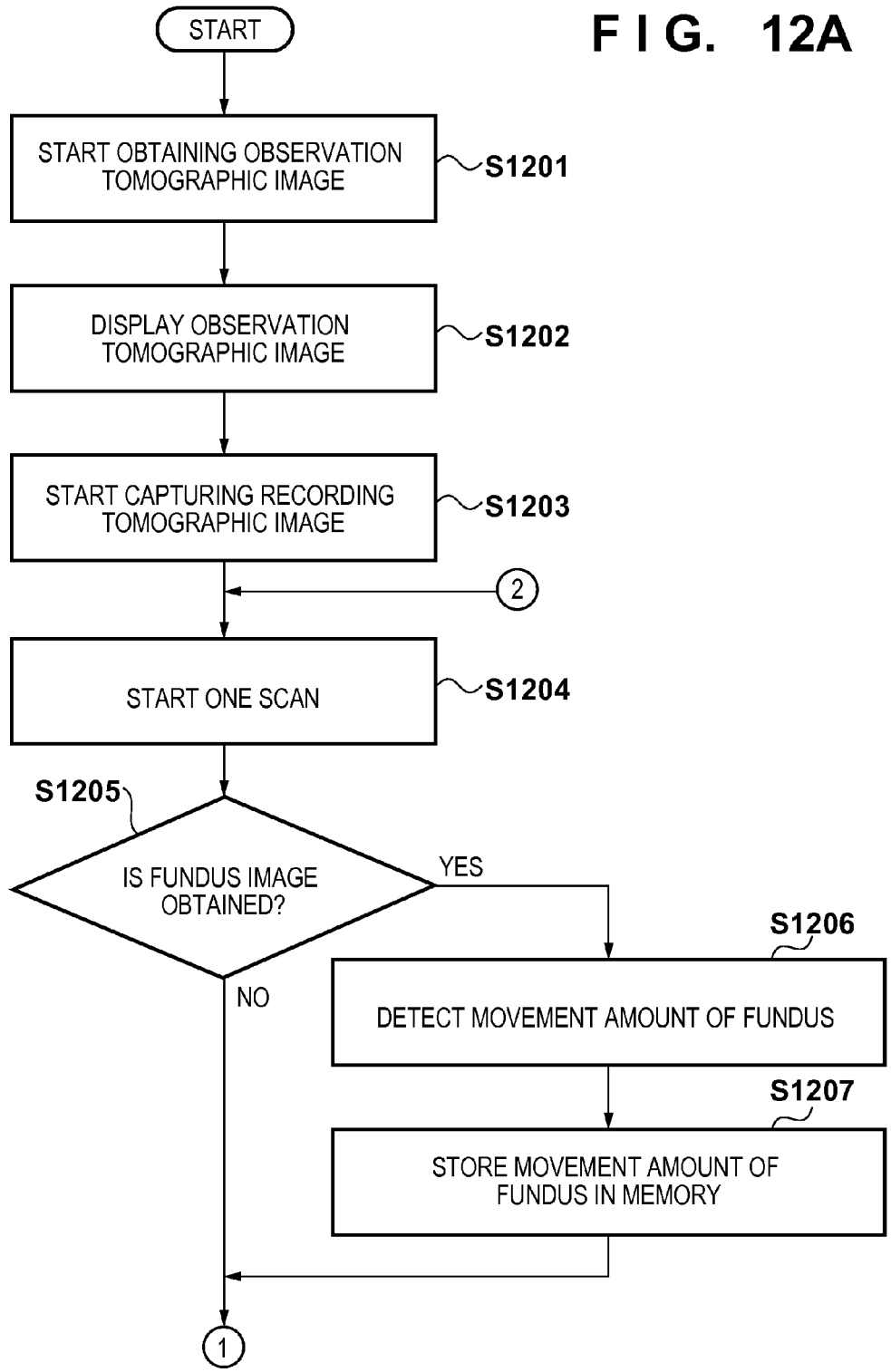
Figure 13:
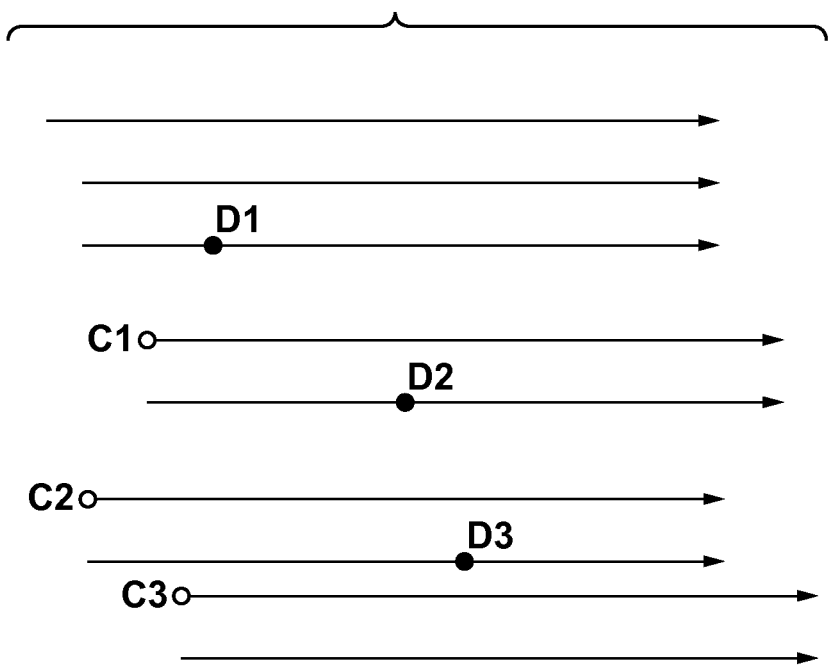
FIG. 13 is a view showing an example of a scan pattern at the time of fundus tracking control.

The apparatus may parallelly execute the automatic alignment stop processing and resume processing described in steps S905 and S907 in FIG. 9 in the processing of the flowcharts of FIGS. 12A and 12B. That is, the apparatus may further execute the alignment stop processing, described in step S905, between the processing in step S1203 and the processing in step S1204, and may further execute the alignment resume processing, described in step S907, between the processing in step S1213 and the processing in step S1214. As described above, the apparatus may execute at least one of the processing associated with automatic alignment in FIG. 9 and the correction processing of the scan position based on fundus tracking in FIGS. 12A and 12B.

Although this embodiment performs control to correct the scan position between the respective scans (between a given scan and the next scan) only when obtaining a recording tomographic image, the apparatus may execute the same control when obtaining an observation tomographic image. In this case, it is possible to reduce the distortion of a retinal layer even in an observation tomographic image. In addition, when obtaining an observation tomographic image, the apparatus may correct the scan position at the time when the movement of the fundus Er is detected, instead of correcting the scan position in the interval between the respective scans (between a given scan and another scan). An observation tomographic image is displayed as a real-time observation moving image, and its display period is very short. Furthermore, since an observation tomographic image is not used for diagnosis, some distortion of a retinal layer can be allowed.

As has been described above, the optical coherence tomographic apparatus according to this embodiment stops at least one of alignment for the optical system for imaging the eye to be examined relative to the eye and the correction of the scan position by fundus tracking on the eye during the execution of a scan. This makes it possible to obtain a tomographic image with little distortion.

(Other Embodiments)

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-014583 filed on Jan. 26, 2012, which is hereby incorporated by reference herein in its entirety.

What is claimed is:

1. An optical coherence tomographic apparatus comprising:
  an obtaining unit configured to obtain a plurality of tomographic images of different respective positions of an eye to be examined based on interfering light obtained by interference between return light from the eye irradiated with measurement light via a scanning unit and reference light corresponding to the measurement light;
  a control unit configured to control the scanning unit such that a scan position is corrected by the scanning unit based on a plurality of images of the eye obtained at different respective times, and a correction of the scan position is performed in an interval between the end of one scan by the scanning unit and the start of a next scan by the scanning unit; and
  a display control unit configured to cause a display unit to display a three-dimensional image in accordance with the plurality of obtained tomographic images under the control of said control unit.

2. The apparatus according to claim 1, wherein said obtaining unit obtains a plurality of fundus images of the eye as the plurality of tomographic images, and
  wherein said control unit controls the scanning unit such that the correction of the scan position is performed based on the plurality of fundus images.

3. The apparatus according to claim 1, wherein said obtaining unit obtains a plurality of anterior ocular segment images of the eye as the plurality of tomographic images, and
  wherein the apparatus further comprises:
  (a) a moving unit configured to move an optical system including an optical path of the measurement light; and
  (b) a unit configured to perform second tracking for the eye by said moving unit based on the plurality of anterior ocular segment images.

4. The apparatus according to claim 1, further comprising a calculation unit configured to calculate an irradiation positional shift of the measurement light relative to the eye based on the plurality of tomographic images,
  wherein said control unit controls the scanning unit such that the correction of the scan position is performed based on the calculated irradiation positional shift.

5. The apparatus according to claim 1, further comprising:
  a positional shift amount calculation unit configured to calculate a positional shift amount of an optical system relative to the eye based on an anterior ocular segment image of the eye and an optical axis position of the optical system; and
  an alignment unit configured to align the optical system relative to the eye based on the positional shift amount,
  wherein said control unit stops the alignment during execution of a recording scan for obtaining an observation tomographic image of the eye and resumes the alignment in a case where the recording scan is complete.

6. The apparatus according to claim 1, wherein said control unit controls the scanning unit such that the correction of the scan position is performed in an interval between one main scan and a next main scan by the scanning unit and the correction of the scan position is not performed during the main scan by the scanning unit.

7. The apparatus according to claim 1, wherein said control unit controls the scanning unit such that the correction of the scan position is performed during a sub-scan by the scanning unit and the correction of the scan position is not performed during the main scan by the scanning unit.

8. The apparatus according to claim 1, wherein said control unit controls the scanning unit such that the correction of the scan position is delayed until the start of the next scan by the scanning unit.

9. An optical coherence tomographic apparatus comprising:
  an image obtaining unit configured to obtain a plurality of anterior ocular segment images of an eye to be examined at different respective times;
  a tomographic image obtaining unit configured to obtain a plurality of tomographic images of the eye at different respective times based on interfering light obtained by interference between return light from the eye irradiated with measurement light and reference light corresponding to the measurement light;
  a moving unit configured to move an optical head unit including an optical path of the measurement light and an optical path of the reference light;
  a unit configured to perform tracking of the eye by said moving unit based on the plurality of anterior ocular segment images; and
  a control unit configured to control an operation of said unit which is configured to perform the tracking to stop a movement of the optical head unit while obtaining a tomographic image for capturing the eye, and to resume the movement of the optical head unit in a case where the obtaining of the tomographic image for a capture is completed.

10. A control method for an optical coherence tomographic apparatus, the method comprising the steps of:
  obtaining a plurality of tomographic images of different respective positions of an eye to be examined based on interfering light obtained by interference between return light from the eye irradiated with measurement light via a scanning unit and reference light corresponding to the measurement light;
  controlling the scanning unit such that a scan position is corrected by the scanning unit based on a plurality of images of the eye obtained at different respective times, and a correction of the scan position is performed in an interval between the end of one scan by the scanning unit and the start of a next scan by the scanning unit; and
  causing a display unit to display a three-dimensional image in accordance with the plurality of obtained tomographic images.

11. The method according to claim 10, wherein in the step of obtaining, a plurality of fundus images of the eye are obtained as the plurality of tomographic images, and
  wherein in the step of controlling, the scanning unit is controlled such that the correction of the scan position is performed based on the plurality of fundus images.

12. The method according to claim 10, wherein in the step of obtaining, a plurality of anterior ocular segment images of the eye are obtained as the plurality of tomographic images, and
  wherein the method further comprises the step of performing second tracking for the eye based on the plurality of anterior ocular segment images using a moving unit configured to move an optical system including an optical path of the measurement light.

13. The method according to claim 10, further comprising the step of calculating an irradiation positional shift of the measurement light relative to the eye based on the plurality of tomographic images, wherein in the step of controlling, the scanning unit is controlled such that the correction of the scan position is performed based on the calculated irradiation positional shift.

14. The method according to claim 10, further comprising the steps of:
calculating a positional shift amount of an optical system relative to the eye based on an anterior ocular segment image of the eye and an optical axis position of the optical system; and
aligning the optical system relative to the eye based on the positional shift amount,
wherein in the step of controlling, the alignment is stopped during execution of a recording scan for obtaining an observation tomographic image of the eye, and the alignment is resumed in a case where the recording scan is complete.

15. The method according to claim 10, wherein in the step of controlling, the correction of the scan position is performed in an interval between one main scan and a next main scan by the scanning unit and the correction of the scan position is not performed during the main scan by the scanning unit.

16. The method according to claim 10, wherein in the step of controlling, the correction of the scan position is performed during a sub-scan by the scanning unit and the correction of the scan position is not performed during the main scan by the scanning unit.

17. The method according to claim 10, wherein in the step of controlling, the scanning unit is controlled such that the correction of the scan position is delayed until the start of the next scan by the scanning unit.

18. A non-transitory computer-readable storage medium storing a program for causing a computer to execute respective steps of a control method for an optical coherence tomographic apparatus of claim 10.

19. A control method for an optical coherence tomographic apparatus, the method comprising the steps of:
obtaining a plurality of anterior ocular segment images of an eye to be examined at different respective times;
obtaining a plurality of tomographic images of the eye at different respective times based on interfering light obtained by interference between return light from the eye irradiated with measurement light and reference light corresponding to the measurement light; performing, based on the plurality of anterior ocular segment images, tracking of the eye by a moving unit which moves an optical head unit including an optical path of the measurement light and an optical path of the reference light; and
controlling an operation in the step of performing the tracking to stop a movement of the optical head unit while obtaining a tomographic image for capturing the eye, and to resume the movement of the optical head unit in a case where the obtaining of the tomographic image for a capture is completed.

20. A non-transitory computer-readable storage medium storing a program for causing a computer to execute respective steps of a control method for an optical coherence tomographic apparatus of claim 19.

21. An optical coherence tomographic apparatus comprising:
a detection unit configured to detect reflection light from an eye to be examined irradiated with light;
a tomographic image obtaining unit configured to obtain a plurality of tomographic images of the eye at different respective times based on interfering light obtained by interference between return light from the eye irradiated with measurement light and reference light corresponding to the measurement light;
a moving unit configured to move an optical system including an optical path of the measurement light and an optical path of the reference light; and
a control unit configured to control said moving unit based on the detected reflection light, and to control said moving unit to stop a movement of the optical system while obtaining a tomographic image for capturing the eye, and to resume the movement of the optical system in a case where the obtaining of the tomographic image for a capture is completed.

22. An optical coherence tomographic apparatus comprising:
an obtaining unit configured to obtain a plurality of tomographic images of an eye to be examined based on interfering light obtained by interference between return light from the eye irradiated with measurement light via a scanning unit and reference light corresponding to the measurement light;
a control unit configured to control the scanning unit such that a scan position is corrected by the scanning unit based on a plurality of images of the eye obtained at different respective times, and the scan by the scanning unit is repeatedly performed in a circle on the eye, and a correction of the scan position is performed in an interval between the end of one scan and the start of a next scan by the scanning unit; and
a display control unit configured to cause a display unit to display a new tomographic image generated by performing addition average processing of the plurality of obtained tomographic images under the control of said control unit.

23. The apparatus according to claim 22, wherein said control unit controls the scanning unit such that the correction of the scan position is delayed until the start of the next scan by the scanning unit.

24. An optical coherence tomographic apparatus comprising:
an obtaining unit configured to obtain a plurality of tomographic images of an eye to be examined at different respective times based on interfering light obtained by interference between return light from the eye irradiated with measurement light via a scanning unit and reference light corresponding to the measurement light; and
a control unit configured to control the scanning unit such that a scan position is corrected by the scanning unit based on a plurality of images of the eye obtained at different respective times, and a correction of the scan position is performed in an interval between the end of one scan and the start of a next scan by the scanning unit after adjusting a difference between an optical path length of the measurement light and an optical path length of the reference light.

25. The apparatus according to claim 24, wherein said control unit controls the scanning unit such that the correction of the scan position is delayed until the start of the next scan by the scanning unit.

26. A control method for an optical coherence tomographic apparatus, the method comprising the steps of:
detecting reflection light from an eye to be examined irradiated with light;
obtaining a plurality of tomographic images of the eye at different respective times based on interfering light obtained by interference between return light from the eye irradiated with measurement light and reference light corresponding to the measurement light;

controlling, based on the detected reflection light, a moving unit to move an optical system including an optical path of the measurement light and an optical path of the reference light, and controlling the moving unit to stop a movement of the optical system while obtaining a tomographic image for capturing the eye, and to resume the movement of the optical system in a case where the obtaining of the tomographic image for a capture is completed.

27. A control method for an optical coherence tomographic apparatus, the method comprising the steps of:
obtaining a plurality of tomographic images of an eye to be examined based on interfering light obtained by interference between return light from the eye irradiated with measurement light via a scanning unit and reference light corresponding to the measurement light;
controlling the scanning unit such that a scan position is corrected by the scanning unit based on a plurality of images of the eye obtained at different respective times, and the scan by the scanning unit is repeatedly performed in a circle on the eye, and a correction of the scan position is performed in an interval between the end of one scan and the start of a next scan by the scanning unit; and
causing a display unit to display a new tomographic image generated by performing addition average processing of the plurality of obtained tomographic images.

28. The control method according to claim 27, wherein in the step of controlling, the scanning unit is controlled such that the correction of the scan position is delayed until the start of the next scan by the scanning unit.

29. A control method for an optical coherence tomographic apparatus, the method comprising:
obtaining a plurality of tomographic images of an eye to be examined at different respective times based on interfering light obtained by interference between return light from the eye irradiated with measurement light via a scanning unit and reference light corresponding to the measurement light; and
controlling the scanning unit such that a scan position is corrected by the scanning unit based on a plurality of images of the eye obtained at different respective times, and a correction of the scan position is performed in an interval between the end of one scan and the start of a next scan by the scanning unit after adjusting a difference between an optical path length of the measurement light and an optical path length of the reference light.

30. The control method according to claim 29, wherein in the step of controlling, the scanning unit is controlled such that the correction of the scan position is delayed until the start of the next scan by the scanning unit.

31. A non-transitory computer-readable storage medium storing a program for causing a computer to execute respective steps of a control method for an optical coherence tomographic apparatus of claim 26.

32. A non-transitory computer-readable storage medium storing a program for causing a computer to execute respective steps of a control method for an optical coherence tomographic apparatus of claim 27.

33. A non-transitory computer-readable storage medium storing a program for causing a computer to execute respective steps of a control method for an optical coherence tomographic apparatus of claim 29.

34. A non-transitory computer-readable storage medium storing a program for causing a computer to execute respective steps of a control method for an optical coherence tomographic apparatus of claim 11.

35. A non-transitory computer-readable storage medium storing a program for causing a computer to execute respective steps of a control method for an optical coherence tomographic apparatus of claim 12.

36. A non-transitory computer-readable storage medium storing a program for causing a computer to execute respective steps of a control method for an optical coherence tomographic apparatus of claim 13.

37. A non-transitory computer-readable storage medium storing a program for causing a computer to execute respective steps of a control method for an optical coherence tomographic apparatus of claim 14.

* * * * *